United States Patent [19]

Levy et al.

[11] Patent Number: 4,900,547
[45] Date of Patent: Feb. 13, 1990

[54] METHOD TO IMMUNIZE MAMMALS AGAINST TUMORS

[75] Inventors: Julia G. Levy, Vancouver; J. Kevin Steele, Victoria; Anthea T. Stammers, Port Coquitlam, all of Canada

[73] Assignee: University of British Columbia, Vancouver, Canada

[21] Appl. No.: 112,974

[22] Filed: Oct. 23, 1987

[51] Int. Cl.$^4$ ..................... A61K 39/00; C07C 103/52
[52] U.S. Cl. ......................................... 424/88; 424/86; 424/87; 424/89; 424/90; 424/91; 424/92; 530/326; 530/327; 530/351; 530/387
[58] Field of Search ....................... 424/88, 86, 87, 89, 424/90, 91, 92; 530/326, 327, 351, 387

[56] References Cited

U.S. PATENT DOCUMENTS 1,365,409 4/1972 Shuurs et al.
1,447,489 2/1984 Murad et al.
4,514,505 4/1985 Canfield et al.
4,545,986 10/1985 Malley ................................. 424/88
4,738,843 4/1988 Oguchi et al. ...................... 424/88

OTHER PUBLICATIONS

Steele et al., "Immumization of DBA/2 Mice with a T cell hybridoma-derived TSF increases immune resistance to the syngeneic" tumors P815 and L12101∞, Journal of Immunolog vol. 137, No. 9, pp. 3025–3030 Nov., 1986.
Steele et al., (1985) Cellular Immunology 90:303–313.

Primary Examiner—Margaret Moskowitz
Assistant Examiner—Abdel A. Mohamed
Attorney, Agent, or Firm—Irell & Manella

[57] ABSTRACT

A general enhancement of the immune system of an animal can be obtained by administration of a T-cell suppressor factor which is idiotypic with regard to any specific antigen when such administration is made in the presence of an effective amount of adjuvant.

5 Claims, No Drawings

METHOD TO IMMUNIZE MAMMALS AGAINST TUMORS

TECHNICAL FIELD

The invention relates to the field of preventing tumor formation in mammals. More particularly, it relates to a method of immunizing a subject against the development of certain tumors.

BACKGROUND ART

In addition to generating antibodies secreted by the B-cell population specific for epitopes associated with them and tumors, like other foreign substances, set in motion certain antigen-specific responses of the lymphatic immune system. In particular, subpopulations of the various T-cell types, including killer (or effector or cytotoxic) cells, helper cells, and suppressor cells are also activated by these tumors. As their names imply, the various subpopulations of T-cells exert effects on each other, presumably through soluble factors collectively known as lymphokines.

The suppressor subpopulation serves as a counterfoil to helper cells with respect to regulating the population of killer cells which are responsible for destroying the foreign material, in this case the tumor. The suppressor population has its own regulation. It appears that there are at least three levels of suppressor cells, each of which secretes one or more soluble (lymphokine) factors which influence other suppressor cells or the killer cell population directly. The mechanisms and materials involved in this cellular communication system are very far from understood, but a current model postulates that in response to stimulation by the antigen, an initial response is made by the secretion of "$TsF_1$" factors by $T_1$ cells, which cells are classified as idiotypic since they are immunocomplementary to the initiating antigen. The $TsF_1$ soluble protein factor(s) may in turn stimulate the secretion of $TsF_2$ soluble protein factor(s) from $T_2$ cells, which because they are presumably complementary to the idiotypic $T_1$ receptors are classified as antiidiotypes. The $TsF_2$ factor(s) in turn may influence $T_3$ cells and contrasuppressor cells, which are thought to have their own factors for communication. A diagramatic representation of this cascade postulated to account for findings thus far obtained is shown below:

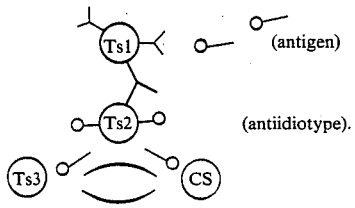

As shown in the above figure, initial stimulation by the antigen produces $TsF_1$ factor from $T_1$ cells, which in turn stimulates $T_2$ cells to secrete $TsF_2$ factors which in turn influence $Ts_3$ and contrasuppressor cells, which secrete their own factors for intercellular communication.

Some work has been done with respect to characterizing some of these cells and factors. A great aid in this work has been the availability of an antibody designated B16G which has been shown to be specific for murine T-suppressor cell factors, murine T suppressor cells, and human T-suppressor factors, but general among these —i.e., it seems to bind to all such factors regardless of their position in the cascade and regardless of the antigen employed to stimulate their secretion (Maier, T.A., et al *J Immunol* (1983) 131:1843; Steele, J.K., et al *J Immunol* (1985) 134:2767; and Steele, J.K., et al *J Immunol* (1985) 135:1201). The preparation of the B16G antibody was described by Maier, T.A., et al *J Immunol* (1983) (supra). This antibody is commercially available from QuadraLogic Technologies, Inc., Vancouver, British Columbia.

With the aid of this antibody as a screening tool, a number of soluble T-suppressors have been identified. Splenocytes and thymocytes in general appear to produce soluble suppressor factors which are immunoreactive with this antibody. In addition, stimulation of $T_1$ cells in response to specific tumor antigens has permitted preparation of hybridoma cell lines which secrete factors in response to these antigens. For example, the A10 cell line is an immortalized $T_1$ suppressor cell line obtained in response to P815 stimulation of murine DBA/2 thymocytes. The preparation of this cell line and characterization of the soluble factors it produces was described in Steele, J.K., et al *J Immunol* (1985) 134:2767 (supra). Analogous hybridoma cell lines have been produced by immortalization of suppressor-T cells obtained in response to injection of ferredoxin *in vivo* (Fd11; ) as described by Steele, J.K., et al *J Immunol* (1986) 137 (in press) A29 cells, a $T_2$ type suppressor cell was obtained by immortalization of T cells of DBA/2 mice immunized with $TsF_1$ preparations obtained from the ascites fluid from growth of the A10 cell line. The production of A29 cells is described by Steele, J.K., et al *J Immunol* (1986) 137 (in press).

Since the precise interrelationship of the soluble factors involved in the suppressor cascade is not at present known, effects of individual factors on the immune system of a subject mammal is to a large extent empirically derived. It has been disclosed that enhancement of the immune system is achieved by administration of a $TsF_2$, as well as by administration of $TsF_1$ factors if administered prior to exposure to a specific antigen against which the immune system is desired to be enhanced. If the $TsF_1$ antigen is administered without adjuvant, the immune system enhancement is specific to the particular antigen with which the $TsF_1$ administered was associated. Thus, it has been shown that when $TsF_1$ obtained from A10 cells is injected without adjuvant into suitable murine subjects, later implantation of P815 tumors is accompanied by an immune response in these animals which exceeds that in animals which were not administered the $TsF_1$ previously. However, syngenic but unrelated tumors, such as L1210 tumors are not affected by this treatment.

In short, preadministration in the absence of adjuvant of the $TsF_1$ associated with a particular tumor type successfully immunizes the subject against that tumor, but not against unrelated tumors. See U.S. Pat. Ser. No. 025,463 filed 13 March 1987 incorporated herein by reference.

It has now been found that if the $TsF_1$ factor preparation is administered prior to tumor implantation in the presence of adjuvant, not only is the animal immunized against growth of the related tumor, but against the growth of other tumors as well. Thus, administration of $TsF_1$ factors in the presence of adjuvant seems to result in a general enhancement of the immune response.

DISCLOSURE OF THE INVENTION

The invention provides a method of stimulating the immune system of mammals and, in particular immunizing mammals against tumor growth. The method comprises administration, in the presence of adjuvant, a soluble $TsF_1$ factor which is secreted by the host cells in response to the administration of tumor antigen. When adjuvant is included in the administration, the immune response is not confined to the specific tumor antigen which stimulated the secretion of the administered factor.

Thus, in one aspect, the invention relates to a method to immunize mammals against tumor growth which comprises administering to a mammalian subject in the presence of an effective amount of adjuvant an effective amount of one or more soluble suppressor proteins of the $TsF_1$ class which $TsF_1$ proteins are secreted in response to tumor antigen. In another aspect, the invention relates to vaccine compositions containing, in unit dosage form, an effective amount of at least one $TsF_1$ in admixture with an effective amount of adjuvant.

MODES OF CARRYING OUT THE INVENTION

The invention is directed to a method to stimulate a generalized enhanced immune response which renders the subject resistant to tumor growth. The method requires administration of $TsF_1$ factor in the presence of adjuvant prior to exposure; hence the procedure should be administered to mammalian subjects perceived by genetic analysis or by family history to be susceptible to tumors or where it is known that exposure to potent carcinogens will occur. The $TsF_1$ factor is injected or otherwise administered using approximately 0.1 ug-1 mg $TsF_1$ factor/kg body weight. For administration, the factors are formulated in a manner commonly utilized for administration of proteinaceous materials in the presence of a suitable adjuvant. Typically, the proteins are administered intravenously and are formulated in, for example, phosphate buffered saline at physiological ionic strength, Ringer solution, Hank's solution, and the like. Suitable formulations for such compounds can be found in *Remington's Pharmaceutical Sciences* latest edition, Mack Publishing Co., Easton, PA.

Suitable adjuvants depend on the species of the subject mammal. Freund's complete adjuvant is suitable for murine and other species; primates, including humans are generally administered adjuvants such as a water in oil emulsion —i.e, Freund's incomplete adjuvant, inorganic gels such as alum, aluminum hydroxide, or aluminum phosphate, polymeric anions such as poly AU, dextran sulfate, and *Bordetella pertussis*. These adjuvants are thought to promote the maintenance of low effective antigen levels in tissues and to assist in the accumulation of macrophages which could bind antigen for reaction with B- and T-cells, as well as to cause proliferation of T-cells.

The $TsF_1$ factors used as antigens are obtained from immortalized cell lines which are prepared using previously disclosed techniques, briefly as follows: a subject mammal is immunized with the appropriate tumor antigen such as P815 antigen in murine tumors, CEA antigen in human tumors, or various tumor associated polysaccharide preparations derived from tumor cell lines or solid tumors. The immunized mammal, which is not necessarily from the same species as that of the tumor antigen, is used as a source of T cells to produce the $TsF_1$ factor. Generally, the spleen is used as a source of desired T-cells, which are then immortalized using, for example, the procedure of Kohler and Millstein or using infection with Epstein Bar Virus. The immortalized cells are then screened for production of the desired $TsF_1$ factor using a protocol which involves immunoreaction with both anti-$TsF_1$ factor antibody and with the tumor antigen. The cell lines obtained in this way are used as sources for the desired proteinaceous $TsF_1$ factor, which is secreted when the cells are cultured in vitro or grown in ascites tumors.

Therefore, while the methods to prepare the hybridomas or other immortalized cells in general are known, critical to obtaining the desired antigen-specific factors of the invention is the proper selection of immunogen —i.e., tumor-associated antigen, and proper design of the screening procedure —i.e., use of the tumor antigen and a T suppressor factor specific antibody.

Thus, using methods similar to those described by Steele, J.K., et al *J Immunol* (1985) 134:2767-2778 (supra), any tumor associated antigen can be used to stimulate the production of T-cells secreting $TsF_1$ factor specific for it. These factors are idiotypic (id+). They can be produced by immortalizing the appropriate T-cells and screening for those which secrete the desired factor. The appropriate criteria are immunoreactivity with the antigen, combined with immunoreactivity with an antibody which is generically reactive with T-cell suppressor factors and specific for them.

A particularly useful antibody in this regard B16G (Maier, T.A., et al *J Immunol* (1983) 131:1843 (supra) is derived from the murine system, but has been shown to be cross-reactive with human $TsF_1$ factors (Steele, J.K., et al *J Immunol* (1985) 135:1201-1206). This antibody has also been shown to be generically reactive to T-suppressor factors regardless of their antigen specificity and regardless of their position in the T-cell cascade. This antibody is commercially available from QuadraLogic Technologies, Vancouver, B.C.

The availability of antibodies useful for screening immortalized T-population for suppressor factors in general eases the production of any particular desired $TsF_1$ component. Thus, a variety of such factors can be prepared so as to be immunoreactive with any desired tumor antigen. By utilizing adjuvant in the method of the invention, the specificity of the $TsF_1$ factor for a particular tumor antigen is retained, although its ability to enhance the immune system to retard tumor growth permits effective protection against a wide range of tumors not limited to that associated with the particular antigen for which the $TsF_1$ factor is specific.

The $TsF_1$ factors generally have molecular weights of 70 kd - 90 kd with subunit molecular weights in the range of 25 kd and 45-50 kd. Further aggregation of the $TsF_1$ factors may occur. The amino terminus of the murine $TsF_1$ factor secreted by A10 has been determined to be:

Val-Lys-Asp-Gly-Asp-Met-Arg-Leu-Ala-Asp-(Asn-Ser-Ser)Ala-Asn(Gln-Gly)Arg-Val-Glu(X)-Tyr-Tyr-Asn:

a smaller 32 kd peptide from A10 has the sequence:

Pro-Lys-Ser-Lys-Glu-Leu-Val-Ser(Lys-Pro)

and contains an internal cyanogen bromide generated peptides of the formula:

Gly-Ile-Ser-Leu-Asn-Met-Leu-Asp-Trp-Arg and of the sequence:

Lys-Pro-Val-Pro-Glu-Lys.

These factors are proteins which are heavily glycosylated and react with antibodies generically specific for T-cell suppressors, such as B16G, as well as with the tumor antigen responsible for their generation. They do not react with antibodies raised against the antigen.

The examples below describe a murine model for immunization of subjects with regard to tumors. Other antigens and other species can also be used. For example, in addition to tumor antigens, antigens associated with bacterial or viral infection may be used to provide the $TsF_1$ factors for immunization. Thus, the method of the invention can also be used to protect against bacterial infection such as those caused by staphlococcus, streptococcus and *E. coli* parasitic infections such as malaria, and virus infections such as hepatitis. The level of cross-species reactivity of the factors themselves is not known, but it is expected to be not insignificant in view of the cross-reactivity of anti-T suppressor antibody with $TsF_1$ factor from a variety of species. It is therefore likely that an intermediate species such as a primate or even rabbits can be used as a source of cells for immortalization to produce factors against tumors of other species which are active in the species bearing the tumor or against infections which are active in alternate species.

EXAMPLES

The following examples are intended to illustrate, but not to limit the invention.

EXAMPLE 1

Preparation of $TsF_1$ Factors From A10 Ascites

As described above, A10 is a T-cell line obtained from DBA mice which secretes a $TsF_1$ factor specific for the P815 tumor antigen and a thyoma AKR cell line BW5147. A10 was grown in CBA×Balb C $F_1$ mice as an ascitic tumor using standard methods. As a control, BW5147 cells were similarly grown.

To obtain the P815 specific $TsF_1$ factor, the factor was prepared from ascites fluid as follows: about 20 ml fresh ascites was applied to a 10 ml B16G-4B Sepharose column at 4° C.; nonadherent material was washed away with PBS until the $OD_{280}$ of the flowthrough fell below 0.01. Material adsorbed to the column was eluted with 0.1 N HCl in 1 ml fractions which were neutralized immediately with 1.5 M Tris-HCl, pH 7.0. The combined fractions containing protein were dialyzed overnight against PBS.

Alternatively, the ascites fluid was purified over P815 membrane-extracted antigen attached to Sepharose 4B in a procedure described by Steele, J.K., et al *J Immunol* (1985) 2767 cited above and incorporated herein by reference.

Analogous purifications were performed on the controls which constituted membrane extracts from $10^8$ BW5147 cells in log phase which had been lysed with 5 ml lysis buffer (0.14 M HCl, 1.5 mM $HCl_2$, 10 mM Tris HCl, 0.1% NP40) centrifuged at 11,500 rpm for 30 min to remove nonsolubilized material, and then the supernatant dialyzed against PBS at 4° C. to remove detergent. The membrane extract is believed to contain material cross-reactive with B16G. Presence of $TsF_1$ factor was verified by ELISA as described by Steele(supra). Four test preparations were thus prepared: control extracts of the membranes of BW5147 cells immunopurified against P815 or B16G and ascites fluid from A10 cells immunopurified with P815 or B16G.

EXAMPLE 2

Immunization of Mice With $TsF_1$

DBA/2 mice, six weeks old, received a subcutaneous injection of 20 mcg of affinity-purified A10 ascites or corresponding fractions of affinity-purified BW5147 membrane extracts or with control PBS solution, all in a 50% emulsion with complete Freund's adjuvant (CFA). The suspensions injected, thus were: A10/P815/CFA; A10/B16G/CFA; BW5147/P815/CFA; BW5147/B16G/CFA; and PBS/CFA.

These preparations were injected 28 days prior to tumor injection (i.e., day—28) and were boosted with an equivalent dose on day—14. The animals were injected subcutaneously at day 0 with $10^4$ P815 cells in the flank at a site far removed from the injection of the foregoing preparations. In the alternative, $10^4$ L1210 tumor cells were injected on day 0. The rate of tumor growth was monitored, and the results recorded in terms of tumor area in $mm^2$.

Both the P815 and L1210 tumors responded to the A10 ascites-derived factor whether purified over P815 or B16G. Both types of tumors also responded to injection by B16G purified factor whether obtained from the A10 cells or the BW5147 extract, which thus apparently itself contains a $TsF_1$ factor, though not a factor specific for P815.

For P815 tumors, mice which had been immunized with A10/P815 purified materials showed a tumor growth to only about 80 $mm^2$ after 11-17 days postinfection, while during the same period, the control injections from BW5147 or PBS showed tumor areas in the range beginning at around 80 $mm^2$ after 11 days to about 120 $mm^2$ after 17. The response of L1210 cells was even more dramatic, the A10 ascites P815/CFA treated animals contained L1210 tumors whose area was maintained at 50 $mm^2$ from day 9–day 14, whereas the two control BW5147/P815/CFA and PBS/CFA groups contained tumors which increased from 50 $mm^2$ on day 9 to 350 $mm^2$ on day 14.

When the B16G purified materials were used, both A10/B16G/CFA and BW5147/B16/CFA maintained tumor growth levels for P815 tumors at around 100 $mm^2$ from day 12–day 17, while the PBS/CFA tumors (P815) increased from about 100 $mm^2$ to 200 $mm^2$ over the same period. For L1210, the tumor area was maintained by both $TsF_1$ preparations at 50 $mm^2$ over day 7–day 14 while the PBS/CFA treated mice had tumors with areas increasing from 50 $mm^2$ to 200 $mm^2$ over the same period.

These results, in terms of survival, rather than tumor size, are shown in Table 1:

TABLE 1

| Immunogen | Challenge with $10^4$ P815 Tumor | | |
|---|---|---|---|
| | No. Animals | Survival Time (days) | Long Term Survivors (100 days free from tumors) |
| PBS/CFA | 8 | 18.3 | 0 |
| BW5147/B16G/CFA | 6 | 23.9 | 0 |
| A10/B16G/CFA | 6 | 24.4 | 1 |
| PBS/CFA | 7 | 34.1 | 0 |

TABLE 1-continued

| Immunogen | Challenge with $10^4$P815 Tumor | | Long Term Survivors (100 days free from tumors) |
|---|---|---|---|
| | No. Animals | Survival Time (days) | |
| *A10/B16G/CFA | 8 | 32.0 | 4 |
| PBS/CFA | 7 | 25.8 | 0 |
| BW5147/Bl6G CFA | 7 | 32.0 | 0 |
| A10/B16G/CFA | 9 | 32.6 | 0 |
| PBS/CFA | 9 | 29.3 | 0 |
| BW5147/P815/CFA | 8 | 29.4 | 0 |
| A10/P815/CFA | 7 | 39.6 | 0 |

*Only $5 \times 10^3$ P815 cells were used in this experiment.

TABLE 2

| Immunogen | Challenge with $10^4$L1210 Tumor | | Long Term Surviors (100 days free from tumors) |
|---|---|---|---|
| | No. Animals | Survival Time (days) | |
| PBS/CFA | 8 | 18.1 | 0 |
| BW5147/B16G/CFA | 8 | 21.0 | 6 |
| A10/B16G/CFA | 6 | 26.0 | 3 |
| PBS/CFA | 10 | 15.7 | 0 |
| BW5147/P815 CFA | 9 | 17.8 | 0 |
| A10/P815/CFA | 0 | 29.9 | 1 |

The influence of A10/P815/CFA and A10/B16/CFA immunization on the immune system was further demonstrated by in vitro mixed lymphocyte reaction (MLR) and cytotoxic lymphocyte generation (CTL) assays. The results from both of these assays indicated that immunization has an enhancing effect on T-cell mediated immune reactions in general. The increased MLR of cells from A10 immunized animals indicates a general nonspecific nature of this treatment; cells of A10 immunized animals give rise to significantly elevated levels of CTL.

We claim:

1. A method to enhance the nonspecific immune response of a mammal to tumors which comprises administering to a subject in need of such enhancement, at a time prior to exposure to tumors to which response is desired, said time effective to enhance said immune response an amount of a $TsF_1$ immunoreactive with a specific tumor effective to enhance said immune response, said administering in the presence of an amount of an adjuvant effective to enhance said immune response.

2. The method of claim 1 wherein the time prior to exposure is between 30 and 5 days.

3. The method of claim 1 wherein the time prior to exposure is between 21 and 7 days.

4. The method of claim 1 wherein the adjuvant is selected from Freund's incomplete adjuvant, alum, and dextran sulfate.

5. A pharmaceutical composition suitable to effect the method of claim 1 which comprises an effective amount of a $TsF_1$ in admixture with an effective amount of adjuvant to stimulate a nonspecific immune response along with at least one pharmaceutically acceptable excipient.

* * * * *